(12) United States Patent
Kobayashi et al.

(10) Patent No.: US 9,839,456 B2
(45) Date of Patent: Dec. 12, 2017

(54) ANTEROLATERAL CALCANEAL PLATE

(71) Applicant: DePuy Synthes Products, Inc., Raynham, MA (US)

(72) Inventors: Kenneth I. Kobayashi, West Chester, PA (US); Mark Siravo, East Norristown, PA (US); Rene Haag, West Chester, PA (US); Sherri Wykosky, Media, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 479 days.

(21) Appl. No.: 14/310,217

(22) Filed: Jun. 20, 2014

(65) Prior Publication Data

US 2015/0366596 A1 Dec. 24, 2015

(51) Int. Cl.
*A61B 17/80* (2006.01)

(52) U.S. Cl.
CPC .......... *A61B 17/8061* (2013.01); *A61B 17/80* (2013.01)

(58) Field of Classification Search
CPC ......... A61B 17/58; A61B 17/68; A61B 17/80; A61B 17/8061; A61B 17/8085
See application file for complete search history.

(56) References Cited

U.S. PATENT DOCUMENTS

| | | | |
|---|---|---|---|
| 6,235,032 B1 | 5/2001 | Link | |
| 7,179,260 B2 | 2/2007 | Gerlach et al. | |
| 7,905,910 B2 | 3/2011 | Gerlach et al. | |
| 7,909,858 B2 | 3/2011 | Gerlach et al. | |
| 8,057,520 B2 * | 11/2011 | Ducharme | A61B 17/8061 606/280 |
| 8,105,367 B2 | 1/2012 | Austin et al. | |
| 8,231,663 B2 | 7/2012 | Kay et al. | |
| 2009/0118768 A1 | 5/2009 | Sixto, Jr. et al. | |
| 2010/0217327 A1 * | 8/2010 | Vancelette | A61B 17/8061 606/281 |
| 2012/0059424 A1 | 3/2012 | Epperly et al. | |
| 2014/0066996 A1 | 3/2014 | Price et al. | |

FOREIGN PATENT DOCUMENTS

| | | |
|---|---|---|
| DE | 202007002190 | 4/2007 |
| EP | 0 920 284 | 9/1999 |
| EP | 2 040 631 | 1/2006 |

* cited by examiner

*Primary Examiner* — Larry E Waggle, Jr.
(74) *Attorney, Agent, or Firm* — Fay Kaplun & Marcin, LLP

(57) ABSTRACT

A plate for treating calcaneal fractures comprises a first portion extending along a first longitudinal axis from a first end to a second end and including a plurality of first openings extending therethrough extending along a second longitudinal axis from the a first end connected to the second end of the first portion to a second end, the first and second portions being angled relative to one another such that, when the plate is positioned along a desired portion of a calcaneus bone, the first and second portions extend parallel to a superior surface of the bone bordering a subtalar joint, the second portion including a plurality of second openings extending therethrough, wherein each of the first and second openings are configured to receive a bone fixation element therein at a user-selected angle relative to a central axis thereof.

12 Claims, 4 Drawing Sheets

US 9,839,456 B2

ANTEROLATERAL CALCANEAL PLATE

BACKGROUND

A fracture of the calcaneus (i.e., heel bone) often results from a fall from a height in which a person lands on his/her feet. Injuries to the calcaneus often damage the subtalar joint, causing the joint to become stiff and making it difficult to walk. Calcaneal fractures may be treated by reducing the fracture and fixing the fracture with screws and/or bone plates. These fixation procedures, however, often require an open surgical reduction and fixation, increasing the risk of dehicense.

SUMMARY OF THE INVENTION

The present invention is directed to a plate for treating calcaneal fractures, comprising a first portion extending along a first longitudinal axis from a first end to a second end and including a plurality of first openings extending therethrough from a first surface of which, when the plate is positioned on the bone in the desired position, faces away from bone, to a second surface which, in the desired position, faces toward the bone and a second portion extending along a second longitudinal axis from the a first end connected to the second end of the first portion to a second end, the first and second portions being angled relative to one another such that, when the plate is positioned along a desired portion of a calcaneus bone, the first and second portions extend parallel to a superior surface of the bone bordering a subtalar joint, the second portion including a plurality of second openings extending therethrough from the first surface to the second surface, wherein each of the first and second openings are configured to receive a bone fixation element therein at a user-selected angle relative to a central axis thereof.

The present invention is also directed to a plate for treating calcaneal fractures, comprising a first portion extending along a first longitudinal axis from a first end to a second end and including a plurality of first openings extending therethrough from a first surface of which, when the plate is positioned on the bone in the desired position, faces away from bone, to a second surface which, in the desired position, faces toward the bone, a second portion extending along a second longitudinal axis from the a first end connected to the second end of the first portion to a second end, the first and second portions being angled relative to one another such that, when the plate is positioned along a desired portion of a calcaneus bone, the first and second portions extend parallel to a superior surface of the bone bordering a subtalar joint, the second portion including a plurality of second openings extending therethrough from the first surface to the second surface, wherein each of the first and second openings are configured to receive a bone fixation element therein at a user-selected angle relative to a central axis thereof, and an extension portion extending laterally from the first portion and including a bone fixation element receiving opening extending therethrough.

DETAILED DESCRIPTION

Figure 1:
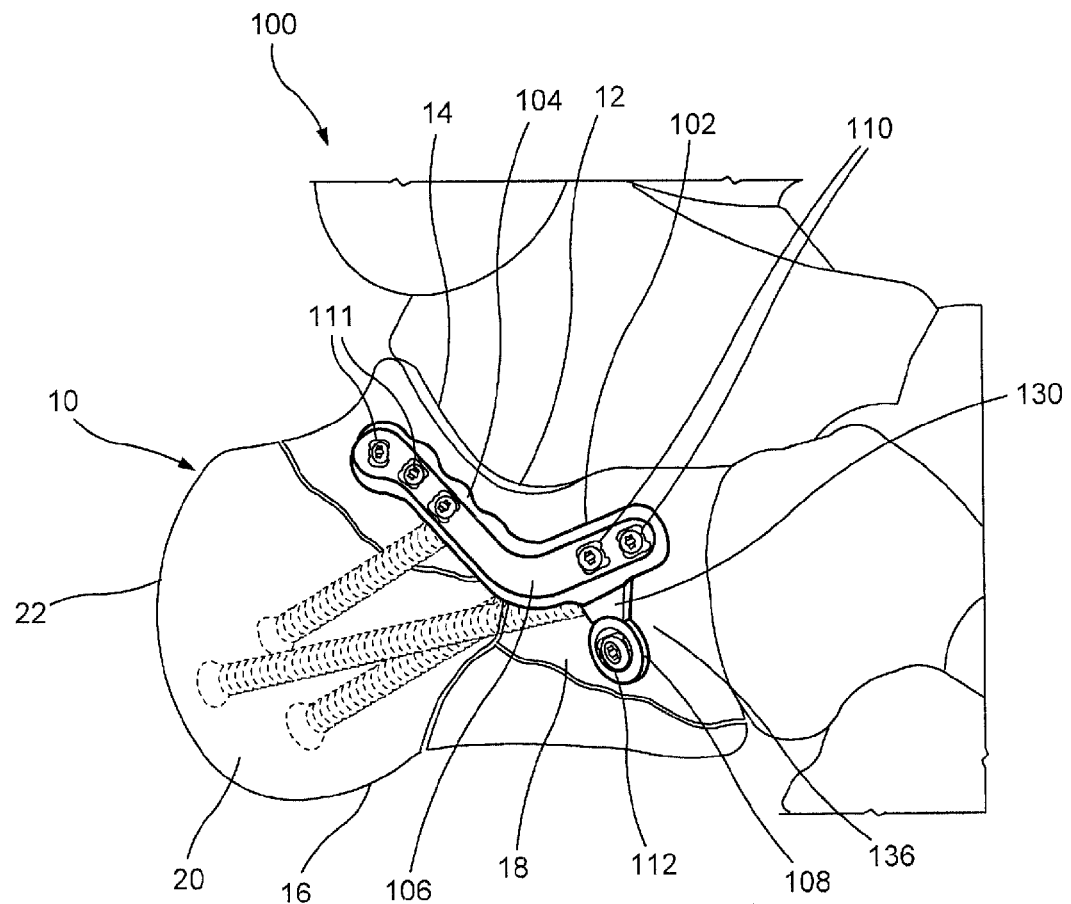
FIG. 1 shows a perspective view of a bone plate according to an exemplary embodiment of the present invention.

The present invention may be further understood with reference to the following description and the appended drawings, wherein like elements are referred to with the same reference numerals. The present invention is directed to a plate for treating fractures and, in particular, to plates for treating calcaneal fractures. Exemplary embodiments of the present invention describe a calcaneal plate including first and second portions extending along first and second longitudinal axes, respectively, angled with respect to one another such that, when the plate is positioned as desired on the bone, the plate extends along a perimeter of a portion of the calcaneus bordering the subtalar joint. Although the exemplary figures depict a plate configured for fixation along a lateral surface of a right calcaneus bone, those of skill in the art will understand that the plates of the present invention may be similarly designed for fixation along a lateral surface of a left calcaneus bone.

Figure 2:
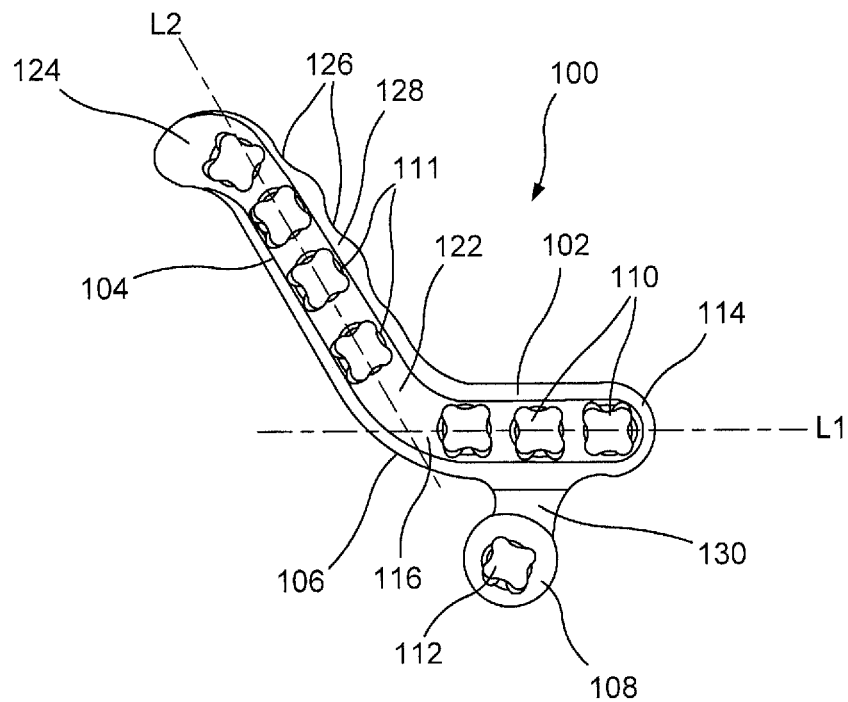
FIG. 2 shows a top plan view of the bone plate of FIG. 1.
Figure 3:
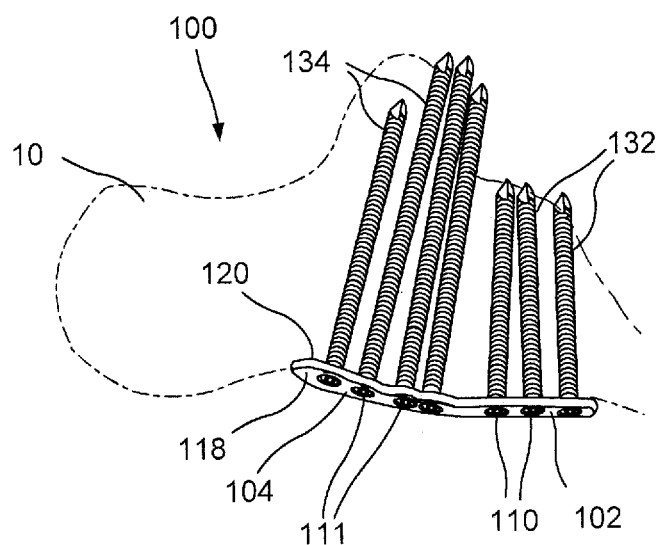
FIG. 3 shows a side view of the bone plate of FIG. 1, fixed to a lateral surface of a bone.

As shown in FIGS. 1-3, a bone plate 100 according to an exemplary embodiment of the invention comprises a first portion 102 extending along a first longitudinal axis L1 and a second portion 104 extending along a second longitudinal axis L2. The first and second portions 102, 104, respectively, are connected to one another via a connecting portion 106. The first and second portions 102, 104 are angled with respect to one another such that an angle between the first and second longitudinal axes substantially corresponds to the Angle of Gissane (e.g, the angle formed by the downward and upward slope of a calcaneal superior surface 14 of a calcaneus bone 10). An angle between the first and second longitudinal axes L1, L2 may be, for example, approximately 120 degrees, but may range from between 100 to 130 degrees. Each of the first and second portions 102, 104 includes a plurality of openings 110, 111, respectively, for receiving bone fixation elements. The bone plate 100 is sized and shaped to be positioned along a portion of a perimeter of a lateral surface of the calcaneus bone 10 bordering the subtalar joint 12 (e.g., parallel to the subtalar joint 12). As those in the art understand, a large number of calcaneal fractures extend from the subtalar joint 12 toward an inferior surface 16 of the calcaneus, fragmenting the bone 10 into an anterior fragment 18 and a posterior bone fragment 20. Thus, the first portion 102 of the plate 100 according to this embodiment is configured to be positioned along a portion of the anterior fragment 18 while the second portion 104 is configured to be positioned along a portion of the posterior fragment 20. The connecting portion 106 of the plate 100 (i.e., a portion of the plate where the first and second portions 102, 104 meet) is configured to be positioned over the fracture line extending from the subtalar joint 12 toward the inferior surface 16 of the bone 10. The plate 100 may further comprise an extension portion 108 extending laterally from the first portion 102 such that, when the plate 100 is in a desired position and orientation along the bone 10, the extension portion 108 extends toward the inferior surface 16 of the bone 10. The extension portion 108 also includes an opening 112 for receiving a bone fixation element.

The first portion 102 extends from a first end 114 to a second end 116 along the first longitudinal axis L1. In an exemplary embodiment, the first portion 102 includes three first openings 110. It will be understood by those of skill in the art, however, that the first portion 102 may include any number of bone fixation element receiving openings therethrough. Each of the first openings 110 extends through the first portion 102 from a first surface 118 of the plate 100 which, when the plate 100 is in an operative position faces away from the bone 10, to a second surface 120 of the plate 100 which, when the plate 100 is in the operative position faces the bone 10. Each of the first openings 110 in this embodiment is a variable angle locking screw hole configured to receive and fix a bone fixation element therein, at any user-selected angle (relative to a central axis of the opening 110), within a predetermined range of angulations. The variable angle locking holes permit bone fixation elements to be inserted therethrough at a desired angle selected to account for a fracture pattern of the bone 10 and/or to target areas of good bone quality. The first openings 110 extend through a portion of the first portion 102 along the first longitudinal axis L1 such that the first openings 110 are aligned relative to one another along the first longitudinal axis L1. Those skilled in the art will recognize that any or all of the first openings 110 may be formed as a standard locking hole or a non-locking hole as desired.

The second portion 104 extends along the second longitudinal axis L2 from a first end 122, connected to the second end 116 of the first portion 102 via the connecting portion 106, to a second end 124. The second portion 104 includes a plurality of second openings 111 extending therethrough from the first surface 118 to the second surface 120. In this embodiment, the second portion 104 includes four second openings 111 extending therethrough. It will be understood by those of skill in the art, however, that the second portion 104 may include any number of openings 111. Each of the second openings 111 in this embodiment is configured as a variable angle locking screw hole configured to receive and fix a bone fixation element therein at any user-selected angle (relative to a central axis of the opening 111), within a predetermined range of angulation. The variable angle locking holes permit bone fixation elements to be inserted therethrough at a desired angle selected to account for a fracture pattern of the bone 10 and/or to target areas of good bone quality. Those skilled in the art will recognize that any or all of the second opening 111 may be formed as a standard locking hole or a non-locking hole as desired.

Two or more of the second openings 111 may extend through portions of the second portion 104 along the second longitudinal axis L2 so that the two or more second openings 111 are aligned relative to one another along the second longitudinal axis L2. In one embodiment, all of the second openings 111 extend through the second portion 104 along the second longitudinal axis L2. In another embodiment, however, the second end 124 of the second portion 104 may be curved slightly relative to the second longitudinal axis L2, toward a tuberosity 22 of the bone 10, so that a second opening 111 extending through the second portion 104 closest to the second end 124 is offset from the second longitudinal axis L2. The second end 124 may also be tapered to facilitate insertion of the plate 100 through a small incision.

The second portion 104 in this embodiment also includes a plurality of optional recesses or scallops 126 along a longitudinal edge thereof 128 which, when the plate 100 is placed in a desired position along the bone 10, faces the subtalar joint 12. The scallops 126 provide clearance for independent screw fixation in a portion of the bone 10 between the longitudinal edge 128 of the plate and the subtalar joint 12. In other words, independent screws placed in this portion of the bone 10 may be received within the scallops 126 to abut a portion of the plate 100.

The connecting portion 106 of the plate 100 may extend along a curve to connect the second end 116 of the first portion 102 to the first end 122 of the second portion 104. As described above, in use, the connecting portion 106 extends over a portion of the bone 10 through which a fracture line typically lies (e.g., from the subtalar joint toward the inferior surface). The connecting portion 106 is free of any openings (e.g., screw holes) to increase a plate strength over this portion of the bone 10.

The extension portion 108 extends laterally from the first portion 102 such that, when the plate 100 is positioned in the desired orientation along the bone 10, the extension portion 108 extends toward the inferior surface of the bone 10. The extension portion 108 in this embodiment includes a single opening 112 extending therethrough. The opening 112 in this embodiment is configured as a variable angle locking hole configured to receive and lock a screw therein at an angle relative to a central axis of the opening 112, within a predetermined range of angulation. The extension portion 108 may include a reduced thickness portion 130 connecting the first portion 102 to a portion of the extension portion 108 including the opening 112. It will be understood by those of skill in the art that the reduced thickness portion 130 facilitates additional contouring of the plate 100 to the contours of the bone 10. Since the opening 112 is offset from the first openings 110 (e.g., the opening 112 is not aligned with the first openings 110 along the first longitudinal axis L1), a surgeon or other user may insert a bone fixation element through the opening 112 of the extension portion 108 to maintain a position of the plate 100 along the bone 10, even when the plate 100 is under load. Those skilled in the art will recognize the extension portion 108 may include any number of openings 112 and that any or all of the openings 112 may be formed as a standard locking hole or a non-locking hole as desired.

According to an exemplary surgical technique utilizing the plate 100, a surgeon or other user makes a small lateral oblique incision along the subtalar joint 12 of a patient to provide visualization of the subtalar joint and aid in reduction of the articular surface. The tapered second end 124 of the second portion 104 is inserted through the incision so that the plate 100 and positioned along the bone 10. It will be understood by those of skill in the art that a user may further contour the plate 100 to correspond to a shape of the bone 10 prior to insertion of the plate 100. In addition, the plate 100 may be pre-contoured (e.g., during manufacturing) to substantially correspond to a surface of the bone 10. As described above, the plate 100 is positioned along the lateral surface of the bone 10 with the first and second portions 102, 104 extending substantially parallel to the subtalar joint 12. The connecting portion 106 may extend across a fracture line of the bone 10. The plate 100 may be provisionally fixed to the bone 10 using wires such as, for example, K-wires or compression wires. The fracture may be reduced using, for example, compression and/or distraction forceps.

Once the fracture has been reduced, as desired, plate 100 may be fixed to the bone 10 by inserting bone fixation elements through some or all of the first and second openings 110, 111 as desired. In one exemplary embodiment, at least five bone fixation elements may be utilized—at least two bone fixation elements through first openings 110 and at least three bone fixation elements through the second openings 111. It will be understood by those of skill in the art, however, that any number of bone fixation elements may be inserted through the openings 110, 111 of the plate 100. A bone fixation element is not required to be inserted into each of the openings 110, 111. The bone fixation elements inserted through the openings 110, 111 may be, for example, variable angle locking screws, metaphyseal screws, or cortex screws. As shown in FIG. 3, each of first bone fixation elements 132 may be inserted through corresponding one of the first openings 110 to buttress an anterior facet of the bone 10 and may be angled in line with the calcaneal-cuboid joint of the bone 10. Each of second bone fixation elements 134 may be inserted through a corresponding one of the second openings 111 such that the second bone fixation elements 134 buttress a posterior and middle facet of the subtalar joint 12 and converge at the sustentaculum of the bone 10. A third bone fixation element 136 may also be inserted through the opening 112 in the extension portion 108, to maintain a position of the plate 100 on the bone 10 even when the plate 100 is under load. The bone fixation elements 132, 134, 136 inserted through the first openings 110, second openings 111 and/or the opening 112 of the extension portion 108 may be angled to target particular fragments of bone or areas of good quality bone. Thus, the bone fixation elements may be inserted through the first and second openings 110, 111 and opening 112 of the extension portion 108 at user-selected angles relative to the central axes thereof. Once the plate 100 has been fixed to the bone 10, as described, above, additional bone fixation elements may be inserted through, for example, the tuberosity 22 of the bone 10 to fix other fractures (e.g., fractures not extending from the subtalar joint 12) of the bone 10, as shown in FIG. 1.

Figure 4:
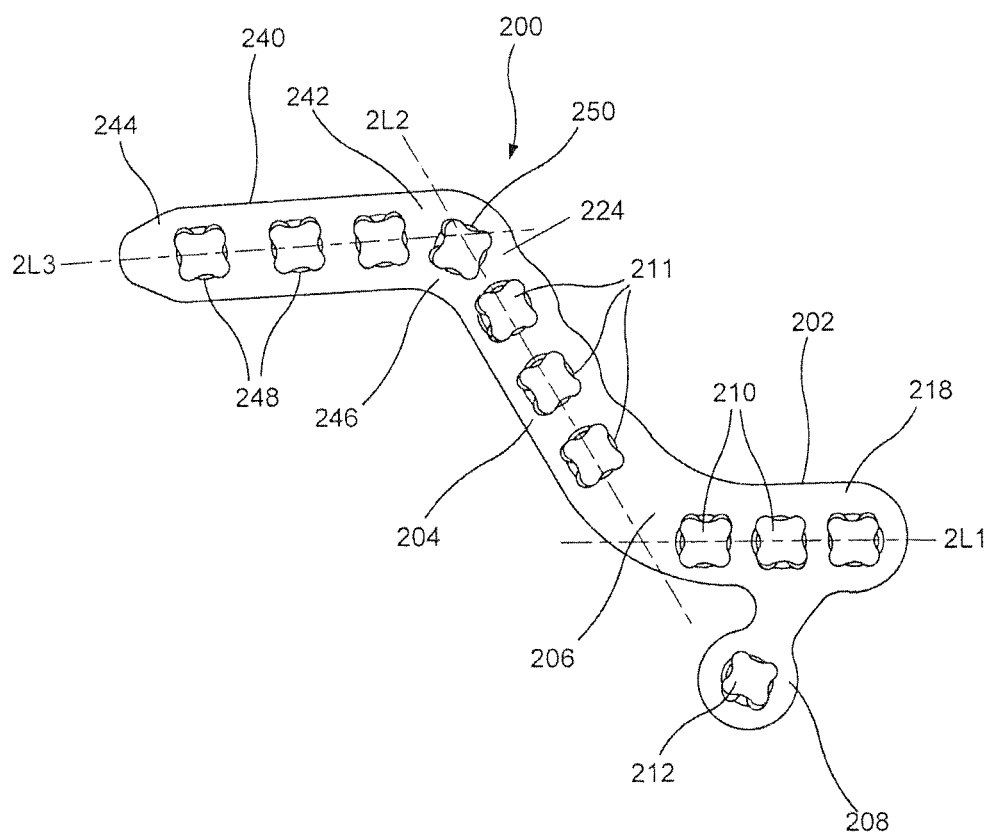
FIG. 4 shows a top plan view of a bone plate according to another exemplary embodiment of the present invention.
Figure 5:
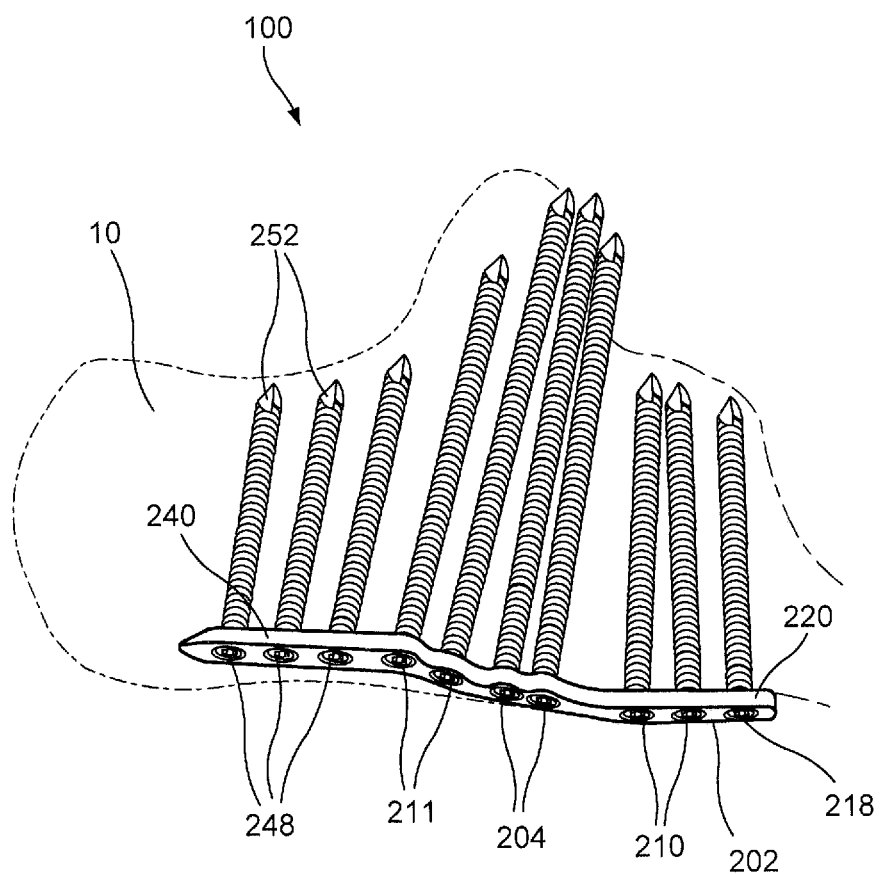
FIG. 5 shows a side of the bone plate of FIG. 4, fixed to a lateral surface of the bone.

As shown in FIG. 4, a bone plate 200 according to a further exemplary embodiment of the invention is substantially similar to the plate 100, described above, comprising a first portion 202 extending along a first longitudinal axis 2L1 and connected to a second portion 204 extending along a second longitudinal axis 2L2 via a first connecting portion 206. As described above in regard to the plate 100, the first and second longitudinal axes 2L1, 2L2 are angled relative to one another to substantially correspond to a slope of the superior calcaneal surface of the subtalar joint 12. Similarly to the plate 100, the plate 200 also comprises an extension portion 208 extending laterally from the first portion 202 such that, when the plate 200 is positioned in the desired orientation along the lateral surface of the bone 10, the extension portion 208 extends toward the inferior surface of the bone 10. The plate 200, however, further comprises a third portion 240 extending along a third longitudinal axis 2L3 from a first end 242 connected to a second end 224 of the second portion 204 to a second end 244. The second end 244 of the plate 200 according to this embodiment is tapered to facilitate insertion of the plate 200 through a small skin incision. The third and second portions 240, 204 may be connected to one another via a second connecting portion 246. The third longitudinal axis 2L3 is angled relative to the second longitudinal axis 2L2 and may be substantially parallel to the first longitudinal axis 2L1. For example, an angle between the third longitudinal axis 2L3 and the second longitudinal axis 2L2 may be between approximately 100 and 140 degrees. In particular, when the plate 200 is positioned along the desired portion of the bone 10 such that the first and second portions 202, 204 border the subtalar joint 12, the third portion 240 extends substantially parallel to a perimeter of the superior surface of the bone 10 along the posterior fragment 20.

Similarly to the first and second portions 102, 104, each of the first and second portions 202, 204 of the plate 200 includes a plurality of first and second openings 210, 211, respectively, extending therethrough from a first surface 218 which, when the plate 200 is in an operative position faces away from the bone 10, to a second surface 220 of the plate 200 which, when the plate 200 is in the operative position faces the bone 10. Similarly to the extension portion 108, the extension portion 208 according to this embodiment also includes an opening 212 extending therethrough. All of the openings 210, 211, 212 in this embodiment may be variable angle holes configured to receive a bone fixation element therethrough at any user-selected angle relative to a central axis of the respective one of the openings 210, 211, 212, within a predetermined range of angulation.

The third portion 240 also includes a plurality of third openings 248 extending therethrough. The third openings 248 according to this embodiment may also be configured as variable angle holes each configured to receive a bone fixation element therethrough at any user-selected (angle relative to a central axis of the opening). In one exemplary embodiment, the third portion 240 includes three third openings 248, each of which extends through the third portion along the third longitudinal axis 2L3 such that the third openings 248 are aligned therealong. The second portion 204 may also include three second openings 211 extending therethrough along the second longitudinal axis 2L2 such that the second openings 211 are substantially aligned therealong. The second connecting portion 246 may also include a connecting portion opening 250 extending therethrough from the first surface 218 to the second surface 220. The connecting portion opening 250 may also be configured as a variable angle hole, but is offset from the third and second openings 248, 211. In other words, the connecting portion opening 250 does not extend through the plate 100 on either of second or third longitudinal axes 2L2, 2L3. Bone fixation elements 252 inserted through the third portion 240 provide additional support along the superior perimeter of the tuberosity 22 of the bone 10.

The plate 200 may be used in a manner substantially similar to the plate 100, described above. The plate 200 is inserted through a small lateral oblique incision along the subtalar joint 12 and positioned on a lateral surface of the bone 10 along a perimeter of a superior surface thereof such that the first portion and second portion 202, 204 extend parallel to the subtalar joint 12 while the third portion 240 extends substantially parallel to the superior surface of the tuberosity 22. The plate 200 is then fixed to the bone 10 via bone fixation elements inserted through any number of the first, second and third openings 210, 211, 248, in a manner substantially similar to the technique described above in regard to the plate 100. A bone fixation element may also be inserted through the extension portion opening 212 to maintain the plate 200 in the fixed position even when the plate 200 is under load.

It will be apparent to those skilled in the art that various modifications may be made in the present invention, without departing from the spirit or scope of the invention. Thus, it is intended that the present invention cover modifications and variation of this invention provided that they come within the scope of the appended claims and their equivalents.

What is claimed is:

1. A plate for treating calcaneal fractures, comprising:
  a first portion extending along a first longitudinal axis from a first end to a second end and including a plurality of first openings extending therethrough from a first surface which, when the plate is positioned on a calcaneus bone in a desired position, faces away from the bone, to a second surface which, in the desired position, faces toward the bone;

a second portion extending along a second longitudinal axis from a first end connected to the second end of the first portion to a second end, the first and second portions being angled relative to one another such that, when the plate is positioned along a desired portion of the bone, the first and second portions extend parallel to a superior surface of the bone bordering a subtalar joint, the second portion including a plurality of second openings extending therethrough from the first surface to the second surface, wherein each opening of the first and second openings defines a central axis, wherein each opening of the first and second openings is configured to receive a bone fixation element therein at a user-selected angle relative to its central axis, and wherein an angle between the first and second longitudinal axes ranges from between 100 and 130 degrees; and an extension portion extending from a longitudinal edge of the first portion so that, when the plate is positioned along the desired portion of the bone, the extension portion extends toward an inferior surface of the bone, the extension portion including a bone fixation element receiving opening extending therethrough.

2. The plate of claim 1, wherein the extension portion includes a reduced-thickness portion between the first portion and the bone fixation element receiving opening.

3. The plate of claim 1, wherein the first and second portions are connected to one another via a first connecting portion for providing support to a portion of the bone through which a fracture extends.

4. The plate of claim 1, further comprising a third portion extending along a third longitudinal axis from a first end connected to the second end of the second portion to a second end, the third longitudinal axis being angled relative to the second longitudinal axis such that, when the plate is in the desired position along the bone, the third portion extends parallel to a portion of the superior surface of a tuberosity of the bone, the third portion including a plurality of third openings extending therethrough from the first surface to the second surface, each of the third openings configured to receive a bone fixation element therein at a user-selected angle relative to a central axis thereof.

5. The plate of claim 4, wherein an angle between the second and third longitudinal axes ranges from between 100 and 140 degrees.

6. The plate of claim 4, wherein the second end of the third portion is tapered to facilitate insertion through a small skin incision.

7. The plate of claim 4, wherein the second and third portions are connected to one another via a second connecting portion including a bone fixation element receiving opening extending therethrough.

8. The plate of claim 1, wherein the first openings extend through the first portion along the first longitudinal axis such that the first openings are substantially aligned therealong.

9. The plate of claim 8, wherein a second opening closest to the second end of the second portion is offset from the second longitudinal axis.

10. The plate of claim 1, wherein two or more of the second openings extend through the second portion along the second longitudinal axis such that the two or more second openings are substantially aligned therealong.

11. The plate of claim 1, wherein the second end of the second portion is tapered to facilitate insertion through a small skin incision.

12. The plate of claim 1, further comprising a plurality of scallops along a longitudinal edge of the second portion, the scallops sized and shaped to receive a portion of a bone fixation element therein.

* * * * *